(12) United States Patent
Krautim et al.

(10) Patent No.: US 8,227,762 B2
(45) Date of Patent: Jul. 24, 2012

(54) DEVICES AND METHODS RELATED TO RADIATION DELIVERY

(75) Inventors: Chawalit Dan Krautim, Lakewood, CA (US); Robert E. Wallace, Los Angeles, CA (US); Matthew Alderson, Long Beach, CA (US)

(73) Assignee: Radiology Support Devices, Inc., Long Beach, CA (US)

( * ) Notice: Subject to any disclaimer, the term of this patent is extended or adjusted under 35 U.S.C. 154(b) by 0 days.

(21) Appl. No.: 13/367,970

(22) Filed: Feb. 7, 2012

(65) Prior Publication Data
US 2012/0134471 A1    May 31, 2012

Related U.S. Application Data

(63) Continuation of application No. 12/957,370, filed on Nov. 30, 2010, now Pat. No. 8,110,811, which is a continuation of application No. 11/924,712, filed on Oct. 26, 2007, now Pat. No. 7,842,929.

(51) Int. Cl.
*G01J 1/42* (2006.01)
*G01N 23/00* (2006.01)
*G01D 18/00* (2006.01)
*A61B 5/08* (2006.01)

(52) U.S. Cl. ........... 250/393; 600/538; 378/18; 378/207

(58) Field of Classification Search .................. 250/393, 250/363.04, 363.03; 378/207, 18, 65; 600/538
See application file for complete search history.

(56) References Cited

U.S. PATENT DOCUMENTS
2005/0211889 A1 * 9/2005 Varchena et al. .......... 250/252.1
* cited by examiner

*Primary Examiner* — David Porta
*Assistant Examiner* — Faye Boosalis
(74) *Attorney, Agent, or Firm* — Moazzam & Associates, LLC

(57) ABSTRACT

Devices and methods are disclosed which relate to the calibration and quality assurance of motion tracking enabled radiation therapy machines. A phantom, capable of mimicking human breathing through inflation and deflation of the lungs, houses an independently moving target (tumor) that detects the amount of radiation received from the radiation therapy machine. This amount can be compared with a desired amount to determine if adjustment or repositioning is necessary. The servo-mechanism(s) of the motion tracking enabled radiation therapy machine(s) are adjusted in comparison of detected versus programmed motion of the respiring phantom having incorporated independently moving target that incorporated radiation dose detector(s). In the invention, motion tracking and irradiation mechanisms of the radiation therapy machine are adjusted to calibrate with reference to performance specifications of the radiation therapy machine.

15 Claims, 6 Drawing Sheets

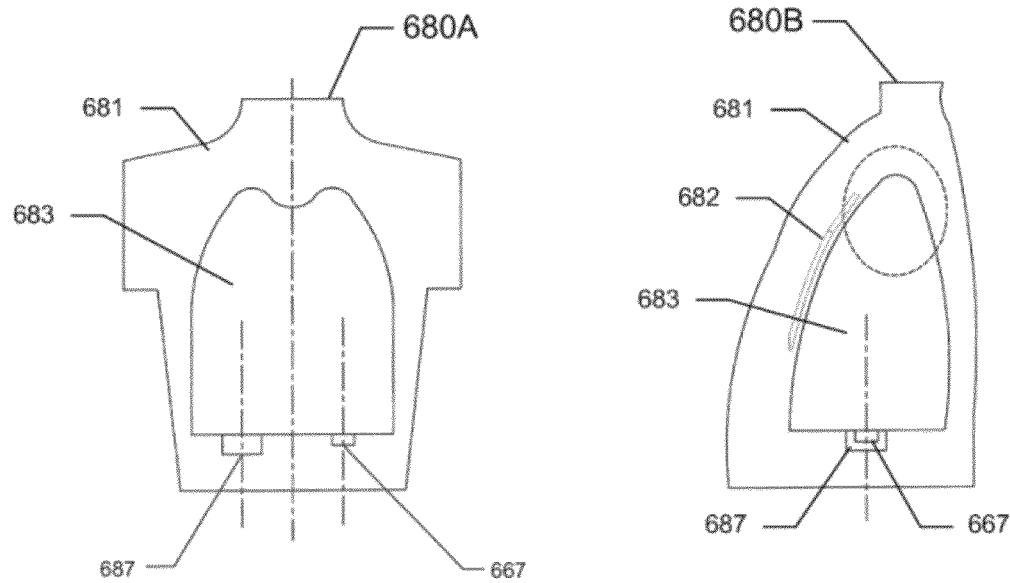
Fig. 6A
Fig. 6B
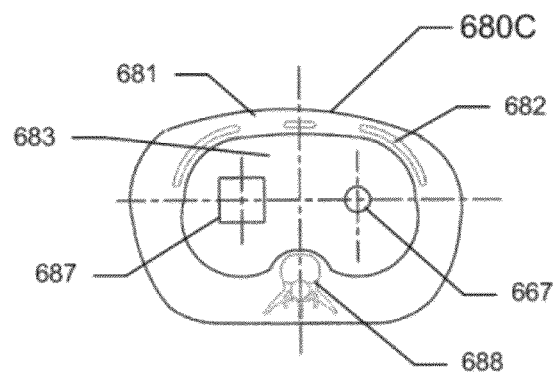
Fig. 6C

DEVICES AND METHODS RELATED TO RADIATION DELIVERY

This application is a continuation of U.S. patent application Ser. No. 12/957,370, filed Nov. 30, 2010, now U.S. Pat. No. 8,110,811; which is a continuation of U.S. patent application Ser. No. 11/924,712, filed Oct. 26, 2007, now U.S. Pat. No. 7,842,929; the contents of which are hereby incorporated by reference herein in their entirety.

BACKGROUND OF THE INVENTION

1. Field of the Invention

The present invention relates to radiation therapy. More particularly, the present invention relates to the calibration and quality assurance of radiation delivery.

2. Background of the Invention

Cancer is a group of diseases in which abnormal cells divide without control, often invading other tissues. According to the American Cancer Society, in 2007 in the United States alone there will have been an estimated 1,444,920 new cases of cancer. It is estimated that in that same period 559,650 people will die in the United States due to various forms of cancer. Many forms of treatment are available and continue to be discovered. One of these forms of treatment is radiation therapy which is used, often in combination with other types of treatment, on roughly half of all cancer sufferers.

Radiation is often utilized in the treatment of cancer in order to control malignant cells and shrink tumors. Due to its harmful effects, physicians often attempt to limit the radiation to other parts of the body. This is accomplished by focusing the radiation on the tumor itself. However, the radiation field often may include normal tissue around the tumor to allow for uncertainties in the position of the tumor. One cause of these uncertainties is the natural movement of organs in the body which cause the position and shape of the tumor to change. Unfortunately, by increasing the field of the radiation, the normal tissue can also be affected. Radiation to these areas may cause side effects during treatment, in a period of time after the treatment, or cumulative side effects from re-treatment. To avoid this result, shaped radiation beams are often aimed from several angles to intersect at the tumor. Because these beams do not change direction with the movement of the tumor, excess radiation is received in a marginal volume around and including the tumor and its possible spatial deformation and positions.

Newer techniques allow for radiation to be aimed such that it follows the movement of the tumor and synchronizes the delivery of the radiation with this movement to limit the excess radiation. The equipment for this process is very complex and even small deviations can have large repercussions. To avoid these deviations, the equipment must frequently be calibrated and the quality of the results must be assured.

In radiation protection, or health physics, a phantom is a device that simulates the human body or part of the human body and is used to calibrate or test the calibration of a detector that measures radiation emanating from within the body. Phantoms can be used in the calibration of radiation delivery devices. However, most phantoms do not provide an accurate representation of the movements internal to the human body and the movement of a tumor within the body. Thus, the calibrations of these radiation delivery devices are not as accurate as they might be particularly with regard to the calibration of systems and methods employed and embodied in these devices to track patient, organ, and tumor/target motions.

In a living human patient, such motions may not always be predictable, having apparently spontaneous variation in rate, depth, etc., due to complex physiological, somatic, and psychological controls. A phantom that can simulate organ and tumor/target movement within the moving body in a more lifelike manner allows the proper calibration and quality assurance of such radiation delivery devices that track organ, tumor/target, and body motion and consequently and programmatically adjust radiation delivery. Furthermore, the organ, tumor/target, and body motion should include both predictable and spontaneous movements to accurately mimic the s of same of an actual human patient.

SUMMARY OF THE INVENTION

The present invention is a phantom that has the ability to mimic the breathing of a living patient by inflating and deflating its lungs. The phantom is realistic in physical and radiographical appearance, action, and composition. A computer hosts control software that communicates with a control interface. This control interface communicates with a pneumatic motion controller. The pneumatic motion controller ultimately controls the moving components of the breathing phantom. The patterns of lung inflation and deflation of the breathing phantom are determined by the control software. The software program generates lung inflation and deflation in simulation of life-like breathing patterns including: coughing, sneezing, singletus, holding breath, and hyperventilation.

In one exemplary embodiment, the present invention is an apparatus for calibrating a motion-tracking enabled radiation therapy machine comprising a synthetic skin in the shape of a body, a synthetic inflatable lung within the skin, and a controller connected to the lung. The controller inflates and deflates the lung to mimic the respiratory movement of a living patient.

In another exemplary embodiment, the present invention is an apparatus for calibrating a motion-tracking enabled radiation therapy machine comprising a body that has substantially similar radiation attenuation properties to that of living tissue, a radiation detector within the body, an inflatable lung within the body, and an inflator attached to the lung, capable of mimicking the respiratory movement of a living patient.

In yet another exemplary embodiment, the present invention is a method of calibrating a motion-tracking enabled radiation therapy machine comprising the steps of testing the radiation therapy machine on a phantom, and adjusting the radiation therapy machine based on the results. The phantom is of the type having an inflatable lung with the ability to mimic respiratory movement of a living patient, and containing a moving target which also may contain a type of device that detects and measures radiation dose and spatial dose distribution.

BRIEF DESCRIPTION OF THE DRAWINGS

FIG. 6A shows a proportional front view of a breathing phantom according to an exemplary embodiment of the present invention.

FIG. 6B shows a proportional side view of a breathing phantom according to an exemplary embodiment of the present invention.

FIG. 6C shows a proportional bottom view of a breathing phantom according to an exemplary embodiment of the present invention.

DETAILED DESCRIPTION OF THE INVENTION

The present invention is a phantom that has the ability to mimic the breathing of a living patient by inflating and deflating its lungs. The phantom is realistic in physical and radiographical appearance, action, and composition. An additional and asynchronous motion is provided for by a target incorporated into the respiring device. Another feature is the application of the invention in the calibration of X-ray and infrared systems used in radiation therapy treatment machines to track the radiation beam with the motion of a target, or tumor, within a moving system. The clinical application of radiation is regional and the present invention is designed to mimic the motion of lung, chest-wall, overlying dermis, and the independent motion of a tumor within a lung. In the invention, these motions are programmatically controlled and may be made similar or dissimilar in predictable fashion. In a living human patient, the motion may not always be predictable, having apparently spontaneous variation in rate, depth, etc., due to complex physiological, somatic, and psychological controls. The invention allows for the predictable simulation of such statistical variations under general program control using standard pseudo-random numerical generation. In the field of radiation use for humans, clinical, research, weapons development, and health physics, such a device is called a phantom, alluding to the mannequin nature of the device. Thus, a feature of this invention is a "breathing phantom."

A "phantom", as used in this disclosure, refers to a device that simulates the human body or part of the human body and is used to calibrate or test the calibration of a radiation therapy machine. A "target", as used in this disclosure, refers to the physical volume within the phantom that acts as a tumor. The target reacts in the presence of radiation, whether by housing radiation detectors, having radiation sensitive material, etc. A "radiation detector", as used in this disclosure, is any device or material that gives a user feedback on the amount of radiation it has received. A radiation detector could be an electronic device that sends readouts to a computer, a material that decays or changes colors when exposed to radiation, or anything else capable of determining levels of radiation.

The invention is comprised of four interacting, communicating systems. A computer 120 hosts control software that communicates with a control interface 140. Control interface 140 communicates with a motion controller 160. Motion controller 160 ultimately controls the moving components of the breathing phantom 180. The patterns of lung inflation and deflation of the breathing phantom is determined by the control software.

Figure 1:
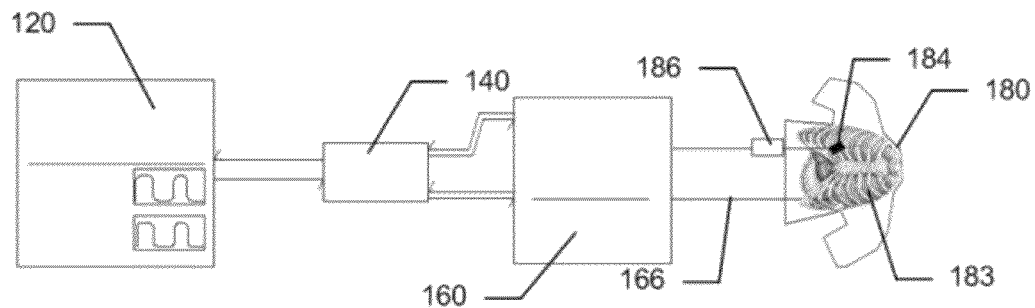
FIG. 1 shows a schematic of a radiation calibration device according to an exemplary embodiment of the present invention.

FIG. 1 shows a schematic of an exemplary embodiment of the present invention. In this embodiment the control computer 120 contains software ultimately used to create movement in the phantom 180. This control computer 120 is connected to a control interface 140 by a connection, such as a USB digital connection, and sends signals through this connection. Alternatively, the connection could be made utilizing any standard or purpose-designed computer digital signaling interface that is capable of maintaining data integrity and communication rates appropriate to the connection. The control interface 140 communicates with an electro-pneumatic motion controller 160, in a feedback control system. This communication includes sending an analog signal to the motion controller 160 in order to create movement in the lungs 183. The control interface's communication with the motion controller 160 also includes sending a signal through the motion actuator 186 to control the target 184. The motion controller 160 provides feedback on the movement of the target 184. The electro-pneumatic motion controller 160 provides regulated air pressure to the lungs 183 of the breathing phantom 180. This is accomplished through a conduit 166, such as an air hose, that is connected to the base of the lungs 183. The motion controller 160 also provides regulated air pressure to the target motion actuator 186. This actuator 186 moves the target 184 in a rectilinear motion. In other embodiments, the actuator 186 also moves the target 184 in rotational or asymmetric or random directions.

Figure 2:
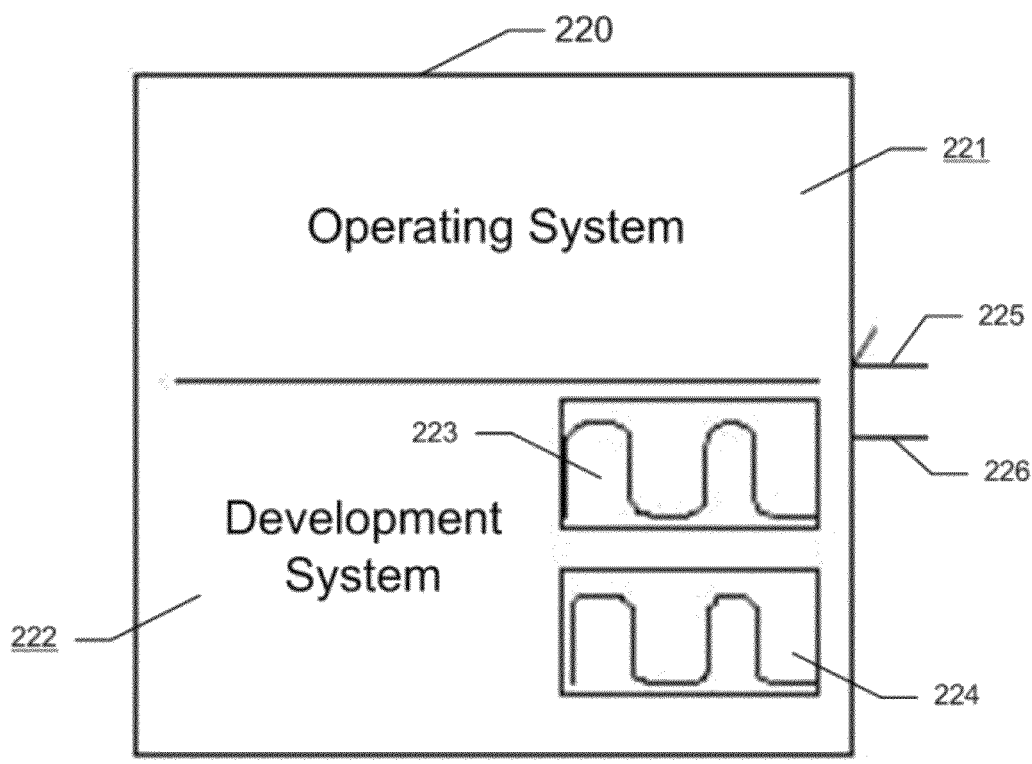
FIG. 2 shows a schematic of a personal computer according to an exemplary embodiment of the present invention.

FIG. 2 shows an exemplary embodiment of the control computer. In this embodiment, the operating system 221 controls software 222 on the control computer 220. This software 222 creates a chest motion waveform 223 and target waveform 224 which will create the desired motions in the phantom. The inputs 225 and outputs 226 allow the control computer 220 to communicate with the control interface.

The personal computer control software includes several components. The operating system 221 of the computer is commercially (or otherwise) available software enabling the discrete and integrated logic of an electronic computer circuit and ancillary systems to perform computational and data processing functions. In the present embodiment, common systems software 221 includes MICROSOFT WINDOWS, LINUX (versions of UNIX), and APPLE COMPUTER CORP'S MAC OS, which provide the platform for an engineering and automation development system 222, such as NATIONAL INSTRUMENTS LABVIEW, in which custom Virtual Instrumentation software is devised for the purpose of automating and controlling the breathing phantom.

Figure 3:
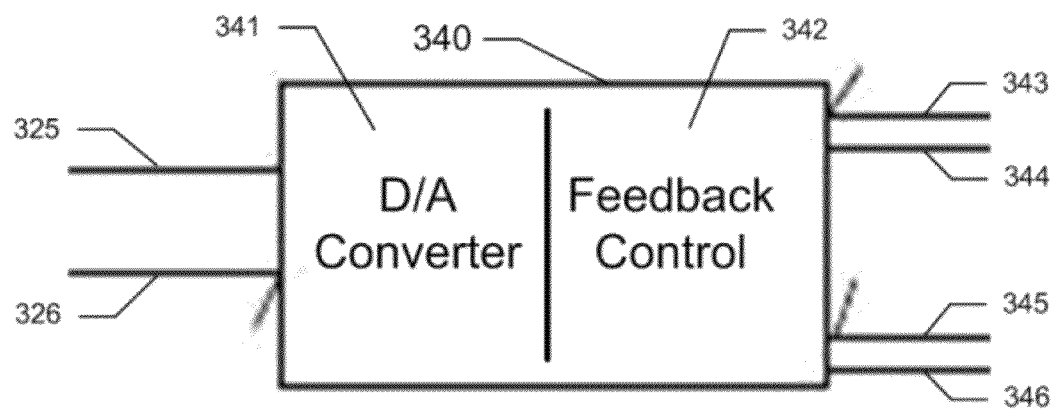
FIG. 3 shows a schematic view of a control interface according to an exemplary embodiment of the present invention.

FIG. 3 shows an exemplary embodiment of the control interface of the present invention. The control interface 340 may be a hardware electronic device that provides signals 344/346 representing the temporal pressure waves that translate into motion of the breathing phantom and target sub-system. The control interface 340 translates, with an onboard Digital to Analog (D/A) converter 341, the programmed digitized waveforms 326 into analog voltage signals. These analog voltage signals 344/346 are interpreted within the electro-pneumatic motion controller sub-system and translated into pneumatic pressure patterns applied to the breathing phantom. The control interface 340 generates control signals for each component, target 344 and lung 346, allowing for independent and uncoupled motion. In practice, these motions will be coupled to simulate a target that is attached to the pleura or chest wall. The control interface 340 provides for the real-time read-back of achieved pressure waveforms from the electro-pneumatic motion controller, allowing servo control. The control interface 340 is realized in an integrated product such as MEASUREMENT COMPUTING CORPORATION, model USB-1208LS, that is comprised of a USB interface (digital Universal Serial Bus standard), digital Input/Output logic, eight channels of Analog to Digital voltage input, and two channels of Digital to Analog conversion for voltage output. The inputs are used to sense and convert signals read-back from the motion controller and the outputs are applied to the motion controller to control pressures applied to the breathing phantom. Analog input and output connections have a range of 0 to 5V direct current. These signals are communicated via standard network cable of Category 5e/6 specification over distances of up to 150 feet.

Figure 4:
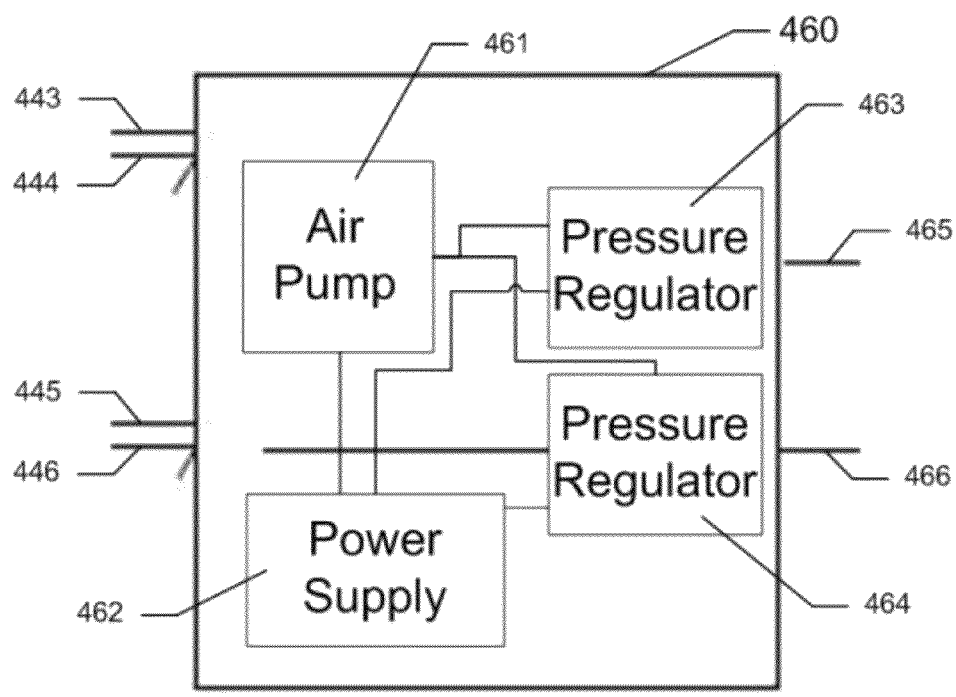
FIG. 4 shows a schematic view of an electro-pneumatic motion controller according to an exemplary embodiment of the present invention.

FIG. 4 shows an exemplary embodiment of an electro-pneumatic motion controller of the present invention. This motion controller 460 is generally comprised of an air pump 461, power supply 462, target pressure regulator 463, and chest motion pressure regulator 464. The motion controller 460 receives signals 444/446 from the control interface. Signals are received for both lung control 446 and target control 444. When these signals 444/446 are received, the power supply 462 supplies power to the air pump 461, chest motion pressure regulator 464, and target pressure regulator 463. The air pump 461 produces air which is regulated by the pressure regulators 463/464. The target pressure regulator 463 sends air pressure through a conduit 465, such as a hose, to the target actuator. The chest motion pressure regulator 464 sends air through a conduit 466, such as a hose, into the lungs of the phantom. The motion controller 460 sends both target feedback 443 and chest motion feedback 445 to the control interface.

In one exemplary embodiment, the electro-pneumatic motion controller 460 is comprised of standard industrial components: a pressurizing air-pump, a 25 Watt, 24 Volt (DC) power supply that powers both electro-pneumatic air pressure regulators for target motion and for lung respiration motion, hose connections communicating pressures controlled by regulators to the breathing phantom target and lung subsystems. The motion controller also has a provision for power inlet from building power at 115 VAC nominal, signal input/output via a Category 5e/6 connector, and pressurized air source ports.

Figure 5A:
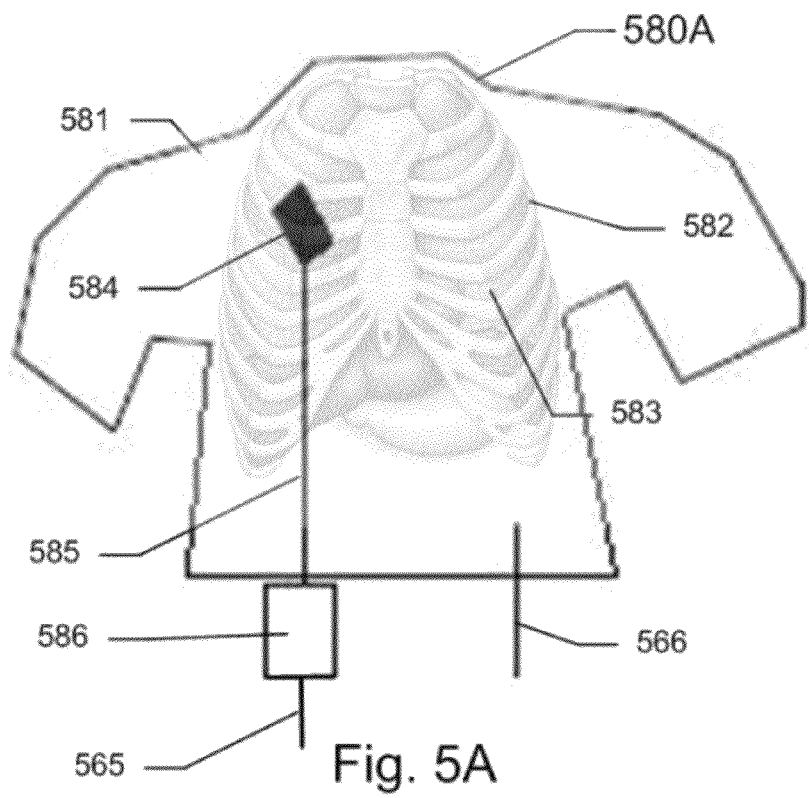
FIG. 5A shows a schematic view of a breathing phantom according to an exemplary embodiment of the present invention.

FIG. 5A shows an exemplary embodiment of a breathing phantom according to an exemplary embodiment of the present invention. In this embodiment, the phantom 580 is generally comprised of a torso with a skin 581, lungs 583, and a target 584. A target motion actuator 586 receives air pressure through a hose 565 from the target pressure regulator. This air pressure is converted to linear motion in an actuator rod 585 which is connected to the target 584 and can move the target 584 within the phantom 580. In other embodiments the air pressure may also be converted to rotational or other desired motion of the actuator rod 585, allowing the target 584 to rotate or perform other motion in addition to the linear movement. The air pressure from the chest motion pressure regulator travels through a hose 566 and into the base of the lungs 583. This air pressure allows the lung 583 to be inflated and deflated to simulate breathing motion.

In one exemplary embodiment of the breathing phantom, the torso mannequin 580 is comprised of a complex plastic simulation of a humanoid torso including lungs 583, ribcage/chest-wall bone 582, skin and sub-dermis 581, and a target 584 within one lung volume. The target 584 is comprised of a sensor holder. This allows for the measurement of radiation using various measuring tools including but not limited to TLD (thermo-luminescent detectors), radiochromic film(s), and telemetric MOSFET detectors which can be positioned within target assemblies of various geometries. With respect to the target actuator 586, the target 584 is attached to the end of the linear actuator moving rod 585. Regulated pressure acts against a return spring to move the target in a nonlinear rate of motion along the axis of the actuator motion. In one embodiment, this is accomplished using an electrically operated linear actuator in which an electrical solenoid acts against a return spring in a similar fashion.

Under the programmed application of increasing and decreasing air pressure, the phantom lungs 583 inflate with air and deflate to replicate human lung respiratory function. As the lungs expand and contract, the simulated ribcage bones 582 also move as does the anterior and antero-lateral skin surface 581. Under the independent programmed application of air pressure to one of several industry standard pneumatic motion actuators 586, target motion within one phantom lung is accomplished in linear, rotational, or combined motions. In one embodiment, the actuator is an SMC CORPORATION model NCQ8B065-125S linear cylinder with pneumatic extension and spring return. In this embodiment, the target motion is linear. Further embodiments utilize an actuator capable of rotating the target or multiple actuators to accomplish both linear and rotational motion. The materials and composition of the phantom are devised to be a faithful simulation of the physical form of a human thorax and to the radiological image properties, such as plastic or elasto-plastic. The particular type of material to be used in this invention would be apparent to one having ordinary skill in the art after consideration of the present disclosure.

Figure 5B:
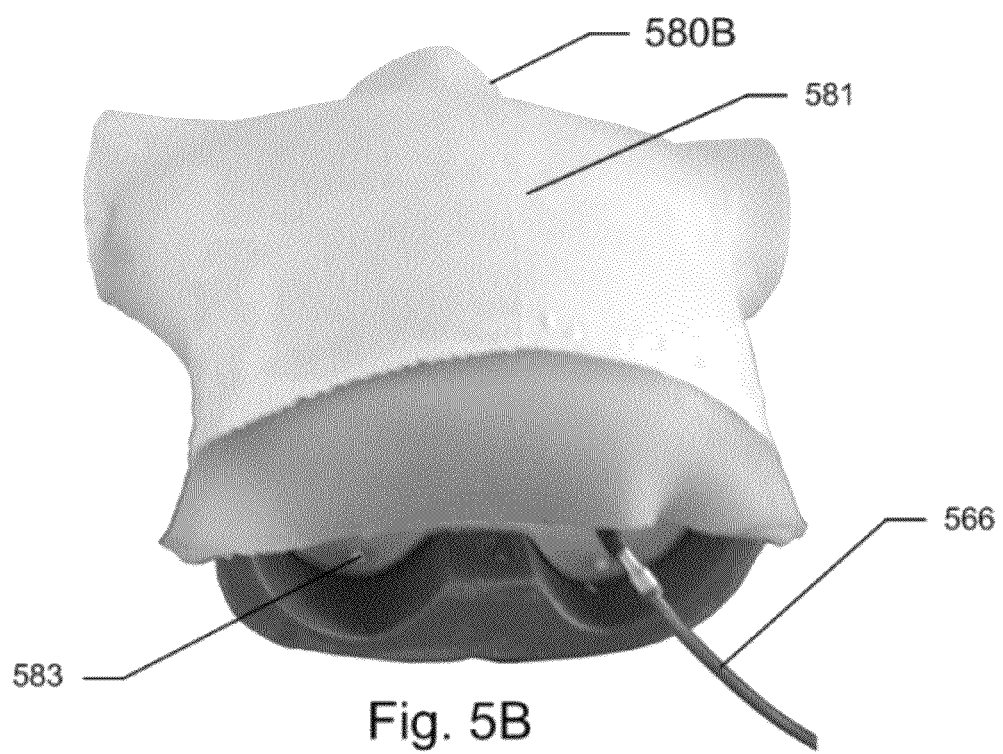
FIG. 5B shows a perspective of a breathing phantom according to an exemplary embodiment of the present invention.

FIG. 5B shows a perspective view of an exemplary embodiment of the breathing phantom. From this view, one can see the skin 581 and sub-dermis. The skin 581 covers the ribcage and chest wall, which house the lungs 583 and target. The air hose 566 can be seen running into the base of the right lung 583, where it delivers air into the lung.

FIG. 6A shows a proportional front view of an exemplary embodiment of the phantom. In this embodiment, the lungs 683 are a single structure. An air port 667 allows the lungs 683 to be inflated and deflated to simulate human breathing. At the same time, an actuator rod (not shown) inserted through the tumor port 687 allows for a target volume to be moved independent of the rest of the phantom 680. In this embodiment, the phantom 680 is covered in a synthetic skin 681 which has similar radiation attenuation properties to that of human skin.

FIG. 6B shows a proportional side view of an exemplary embodiment of the phantom. In this embodiment, the ribs 682 are located adjacent to the lungs 683 and above the air port 667 and tumor port 687. The air port 667 and tumor port 687 are approximately centered with respect to the side of the lungs 683.

FIG. 6C shows a proportional bottom view of an exemplary embodiment of the phantom. In this embodiment, the tumor port 687 and air port 667 are approximately centered on the bottom of the lungs 683. The ribs 682 and spinal column 688 allow for a more human like simulation as they will affect the travel of radiation into the phantom 680.

Figure 7:
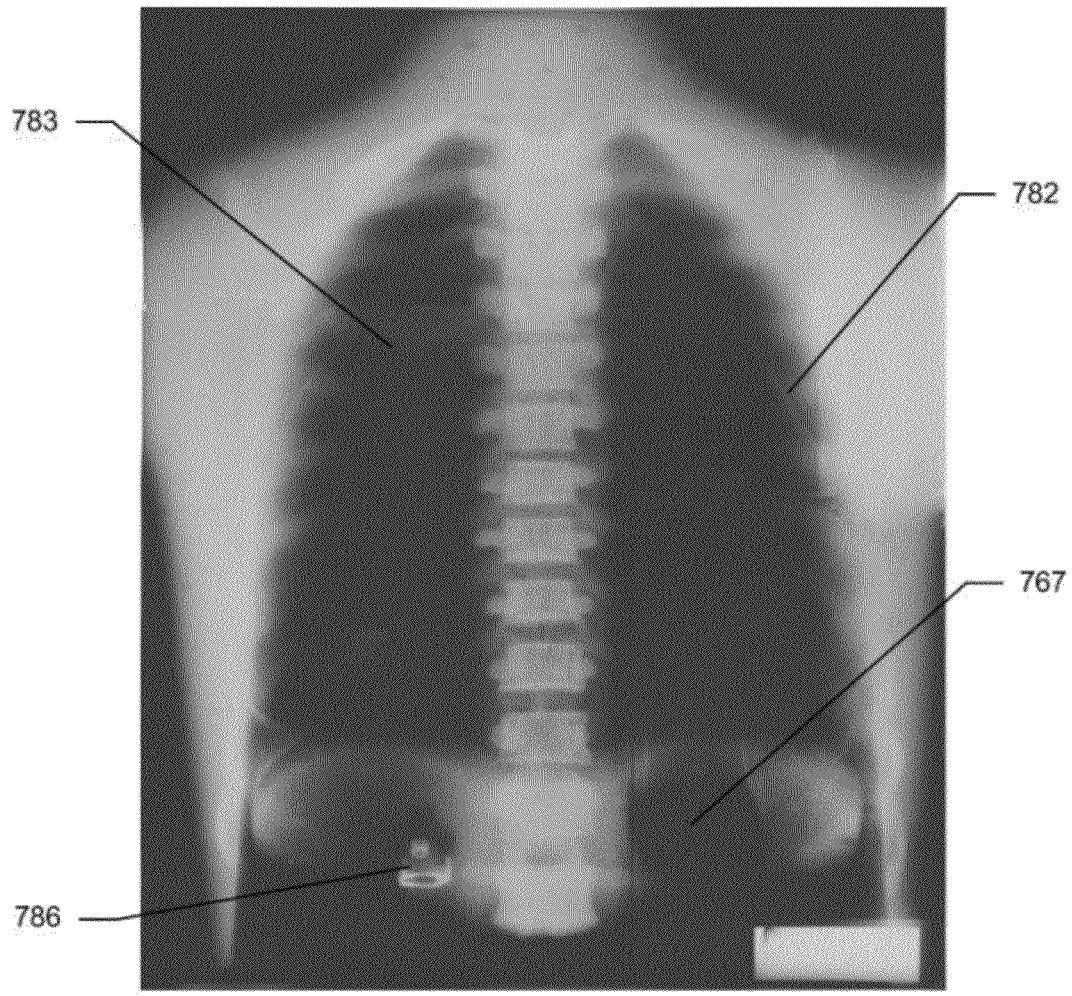
FIG. 7 shows an X-ray of a breathing phantom according to an exemplary embodiment of the present invention.

FIG. 7 shows a transmission radiograph x-ray examination of an embodiment of the present invention. This x-ray shows a device that looks similar to a human thorax. A cross-sectional image set using x-ray computed tomography provides the same result. This remains true during programmed motion(s). From the x-ray, one can see the lung volumes 783, as well as the air port 767 at the bottom of one lung (e.g., right lung) where it connects to the air hose. The springs and metal pieces from the target actuator 786 can be seen towards the bottom of the other lung (e.g., left) 783. The ribcage 782 and a backbone can be seen as well.

Figure 8:
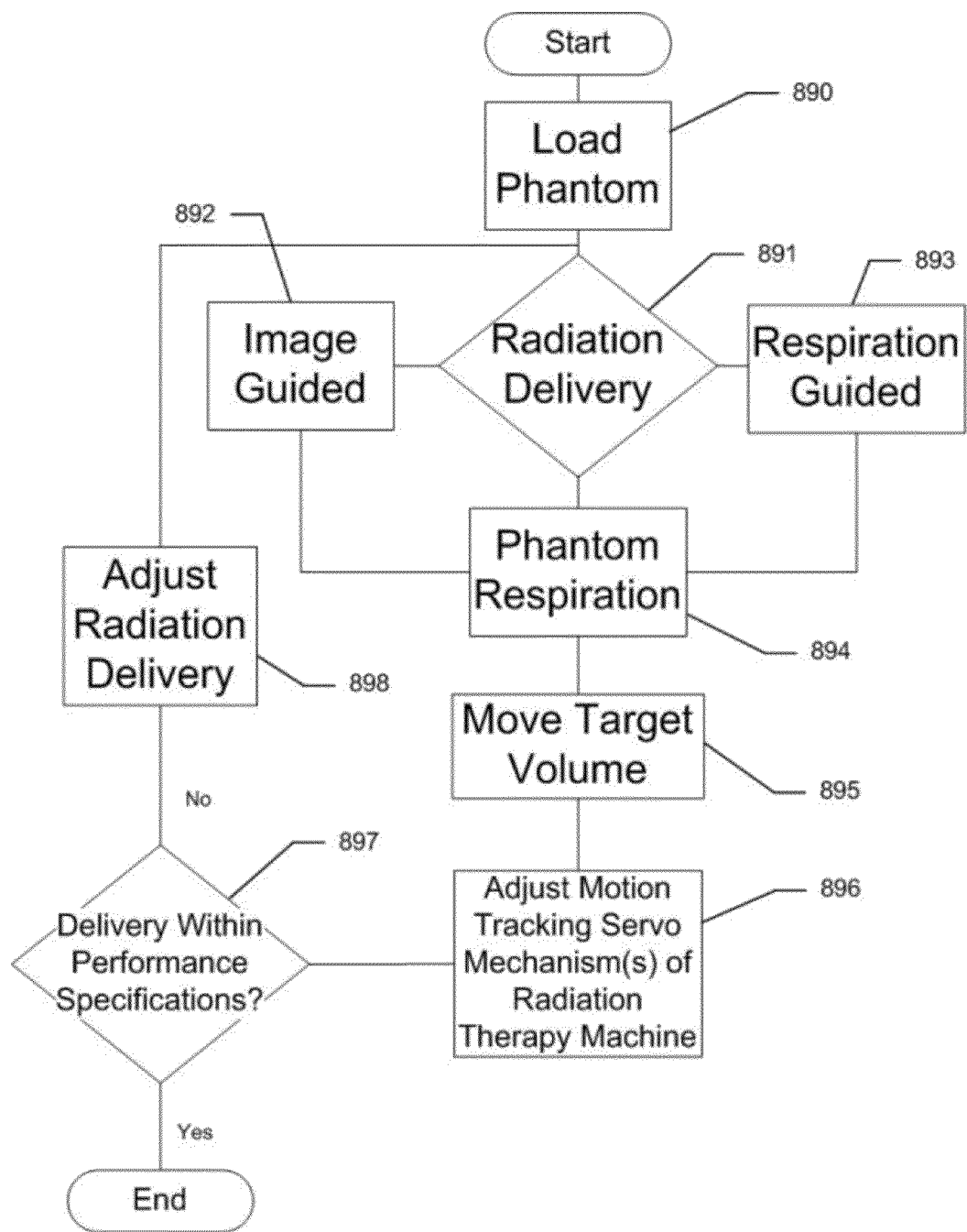
FIG. 8 shows a flow chart for a radiation calibration method according to an exemplary embodiment of the present invention.

FIG. 8 shows a method of using the phantom to calibrate a radiation therapy machine according to one exemplary embodiment. The method first entails loading a breathing phantom 890 onto a radiation therapy machine. Radiation is then delivered 891 to a target within the phantom. This could be accomplished using respiration guided radiation delivery 893 or image guided radiation delivery 892. During the radiation delivery, the lungs of the phantom inflate and deflate 894, mimicking the breathing of a human. This will cause movement in the target. However, at this same time, the user can choose whether to independently move the target 895. During radiation delivery, the radiation therapy machine systems and methods track phantom respiratory and target motions to provide servo-controlled adaptation of radiation delivery to the motion(s). During the radiation delivery and during phantom and target motions, the radiation therapy machine servo mechanisms are adjusted 896 to match the known phantom and target motions and predictions of expected radiation dose measures. If the radiation delivery performance is within performance expectations 897, the process terminates. If radiation delivery performance specifications are not met, however, the radiation delivery system is re-calibrated 898. After re-calibration 898, the sequence of events will start again, with delivery of radiation 891.

The described four component system is but one exemplary embodiment of the breathing phantom invention. Other embodiments would be identifiable by one versed in the field of humanoid simulation for radiological applications and in the allied fields of industrial and laboratory control and automation.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for simulating movement of a tumor in a human body, the system comprising:
   a computer including a memory, a processor, and logic on the memory, the logic including instructions for:
   generating a first waveform representative of a motion of a breathing phantom, the breathing phantom including a body containing a lung, and
   generating a second waveform representative of a motion of a target, the target being placed within the lung, the motion of the target being independent from the motion of the breathing phantom; and
   a control interface for receiving the first and second waveforms and for converting the first and second waveforms into corresponding motion signals for the breathing phantom and the lung.

2. The system of claim 1, further comprising a motion controller for providing regulated air pressure to the lung according to a first signal from the control interface; wherein the regulated air pressure provided to the lung causes the lung to inflate and deflate to simulate breathing.

3. The system of claim 2, wherein the body further includes a simulation of a ribcage, skin, and sub-dermis.

4. The system of claim 3, wherein the ribcage, skin, and sub-dermis move due to the inflation and deflation of the lung.

5. The system of claim 2, wherein the motion controller is an electro-pneumatic motion controller.

6. The system of claim 5, wherein the electro-pneumatic motion controller provides the regulated air pressure to the lung through a conduit connected to a base of the lung.

7. The system of claim 2, wherein the motion controller further comprises:
   an air pump;
   a power supply;
   a target pressure regulator; and
   a chest motion pressure regulator,
   wherein, when the first signal is received from the control interface, the power supply supplies power to the air pump, the chest motion pressure regulator, and the target pressure regulator.

8. The system of claim 1, further comprising a motion actuator that moves the target according to a second signal from the control interface.

9. The system of claim 8, wherein the motion actuator moves the target in at least one of a rotational direction and an asymmetric direction.

10. A method for simulating movement of a tumor in a human body, the method comprising:
    generating a first waveform representative of a motion of a breathing phantom, the breathing phantom including a body containing a lung;
    generating a second waveform representative of a motion of a target, the target being placed within the lung, the motion of the target being independent from the motion of the breathing phantom; and
    transmitting the first and second waveforms to a motion controller to be respectively converted into motion of the breathing phantom and the target.

11. The method of claim 10, further comprising delivering radiation to the target.

12. The method of claim 11, further comprising adjusting the delivery of the radiation accordingly to match the motions of the breathing phantom and the target in order to deliver radiation to the target.

13. The method of claim 10, wherein the lung is inflated and deflated using an electro-pneumatic motion controller.

14. The method of claim 10, wherein the target is moved using a target actuator.

15. A computer program product stored on a computer-readable medium, the computer program product for simulating movement of a tumor in a human body and comprising instructions for:
    generating a first waveform representative of a motion of a breathing phantom, the breathing phantom including a body containing a lung;

generating a second waveform representative of a motion of a target, the target being placed within the lung, the motion of the target being independent from the motion of the breathing phantom; and transmitting the first and second waveforms to a motion controller to be respectively converted into motion of the breathing phantom and the lung.

* * * * *